(12) United States Patent
Damadian et al.

(10) Patent No.: US 7,030,612 B1
(45) Date of Patent: Apr. 18, 2006

(54) BODY REST FOR MAGNETIC RESONANCE IMAGING

(75) Inventors: Jevan Damadian, East Northport, NY (US); William H. Wahl, Smithtown, NY (US)

(73) Assignee: Fonar Corporation, Melville, NY (US)

( * ) Notice: Subject to any disclaimer, the term of this patent is extended or adjusted under 35 U.S.C. 154(b) by 0 days.

(21) Appl. No.: 10/756,576

(22) Filed: Jan. 13, 2004

(51) Int. Cl.
*G01V 3/00* (2006.01)

(52) U.S. Cl. .................................. 324/318; 600/415

(58) Field of Classification Search ................ 324/318, 324/319, 320, 322, 300; 600/415, 421, 422, 600/425
See application file for complete search history.

(56) References Cited

U.S. PATENT DOCUMENTS

| | | | |
|---|---|---|---|
| 4,411,270 A | 10/1983 | Damadian | |
| 4,534,076 A | 8/1985 | Barge | |
| 4,534,358 A | 8/1985 | Young | |
| D283,858 S | 5/1986 | Opsvik | |
| 4,614,378 A | 9/1986 | Picou | |
| 4,767,160 A | 8/1988 | Mengshoel et al. | |
| 4,770,182 A | 9/1988 | Damadian et al. | |
| 4,924,198 A | 5/1990 | Laskaris | |
| 5,008,624 A | 4/1991 | Yoshida | |
| 5,065,761 A | 11/1991 | Pell | |
| 5,153,546 A | 10/1992 | Laskaris | |
| 5,155,758 A | 10/1992 | Vogl | |
| 5,251,961 A | 10/1993 | Pass | |
| 5,349,956 A * | 9/1994 | Bonutti | 600/425 |
| 5,436,607 A | 7/1995 | Chari et al. | |
| 5,475,885 A | 12/1995 | Ishikawa | |
| 5,640,958 A | 6/1997 | Bonutti | |
| 5,680,861 A | 10/1997 | Rohling | |
| 5,772,595 A * | 6/1998 | Votruba et al. | 600/415 |
| D417,085 S | 11/1999 | Kanwetz, II | |
| 6,011,396 A | 1/2000 | Eckels et al. | |
| 6,385,481 B1 | 5/2002 | Nose et al. | |
| 6,411,088 B1 | 6/2002 | Kuth et al. | |
| 6,424,854 B1 | 7/2002 | Hayashi et al. | |
| 6,504,371 B1 | 1/2003 | Damadian et al. | |
| 6,611,703 B1 * | 8/2003 | Kuth et al. | 600/415 |
| 6,639,406 B1 | 10/2003 | Boskamp et al. | |
| 6,677,753 B1 | 1/2004 | Danby et al. | |
| 2001/0029330 A1 | 10/2001 | Nose et al. | |
| 2002/0013524 A1 | 1/2002 | Hayashi et al. | |
| 2002/0032927 A1 | 3/2002 | Dinkler | |

FOREIGN PATENT DOCUMENTS

| | | |
|---|---|---|
| JP | 63-68157 | 3/1998 |
| WO | WO-97/17896 | 5/1997 |

OTHER PUBLICATIONS

U.S. Appl. No. 10/419,385.
U.S. Appl. No. 10/131,843 filed Apr. 25, 2002.

* cited by examiner

*Primary Examiner*—Louis Arana
(74) *Attorney, Agent, or Firm*—Lerner, David, Littenberg, Krumholz & Mentlik, LLP (57) ABSTRACT

System, apparatus and method for performing magnet resonance imaging. The apparatus comprises first and second members for distributing the weight of a patient to be imaged in a substantially upright position between the patient's knees and buttocks. The system comprises a horizontal field magnet magnetic resonance imaging apparatus in combination with the apparatus. In accordance with the method a patient is imaged in an ergonomic position with the patient's weight distributed between the patient's buttocks and knees.

37 Claims, 10 Drawing Sheets

BODY REST FOR MAGNETIC RESONANCE IMAGING

BACKGROUND OF THE INVENTION

The present invention relates to magnetic resonance imaging systems, apparatus and procedures.

In magnetic resonance imaging ("MRI"), an object to be imaged, as for example, a body of a human subject, is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the precessing automic nuclei to rotate or "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are the dominant factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Several factors affect the positioning of patients and ancillary equipment in MRI imaging. Many MRI magnets use one or more solenoidal superconducting coils to provide the static magnetic field arranged so that the patient is disposed within a small tube running through the center of the magnet. The magnet and tube typically extend along a horizontal axis, so that the long axis or head-to-toe axis of the patient's body must be in a horizontal position during the procedure. Moreover, equipment of this type provides a generally claustrophobic environment for the patient.

Iron core magnets have been built to provide a more open environment for the patient. These magnets typically have a ferromagnetic frame with a pair of ferromagnetic poles disposed one over the other along a vertical pole axis with a gap between them for receiving the patient. The frame includes ferromagnetic flux return members such as plates or columns extending vertically outside of the patient-receiving gap. A magnetic field is provided by permanent magnets or electromagnetic coils associated with the frame. A magnet of this type can be designed to provide a more open environment for the patient. However, it is still generally required for the patient to lie with his or her long axis horizontal. This affects the conditions under which imaging may be performed and also affects the comfort level of the patient.

Recently, magnets having horizontal pole axes that provide an open patient environment have been developed. As disclosed, for example, in commonly assigned U.S. Pat. No. 6,414,490 ("the '490 patent"), which is a continuation of U.S. patent application Ser. No. 08/978,084, filed on Nov. 25, 1997, and in co-pending, commonly assigned U.S. patent application Ser. No. 09/718,946 ("the '946 application"), filed on Nov. 22, 2000, the disclosures of which are incorporated by reference herein, a magnet having poles spaced apart from one another along a horizontal axis provides a horizontally oriented magnetic field within a patient-receiving gap between the poles. Such a magnet can be used with a patient positioning device including elevation and tilt mechanisms to provide extraordinary versatility in patient positioning. For example, where the patient positioning device includes a bed or similar device for supporting the patient in a recumbent position, the bed can be tilted and/or elevated so as to image the patient in essentially any position between a fully standing position and a fully recumbent position, and can be elevated so that essentially any portion of the patient's anatomy is disposed within the gap in an optimum position for imaging. As further disclosed in the aforesaid patent and patent applications, the patient positioning device may include additional elements such as a platform projecting from the bed to support the patient when the bed is tilted towards a standing orientation. Still other patient supporting devices can be used in place of a bed in a system of this type. For example, a seat may be used to support a patient in a sitting position. Thus, magnets of this type provide extraordinary versatility in imaging.

The position of a patient during magnetic resonance imaging may affect or limit the imaging information obtained. A patient may exhibit a symptom if oriented in an upright or weight bearing position and no symptom if oriented in a recumbent or horizontal position. For example, it may be necessary to image a patient in an upright or gravity bearing position to discern a symptom and provide a diagnosis relating to the neck, spine, hip, knee, foot or ankle areas of the human anatomy.

In addition to a patient's position, movement by a patient during imaging may also affect the images obtained. In fact, magnetic resonance imaging procedures generally require the patient to remain as still as possible during imaging. A patient positioned in a weight-bearing upright posture may find it more difficult to remain still during imaging. The anxiety level of a patient is another factor that may affect how still a patient remains during imaging. In general, those magnets that place the patient in the bore of the magnet during imaging tend to add to the patient's anxiety level because of the closed-in and tight environs. A more relaxed patient tends to move less during imaging.

Of utility then are apparatus and methods that enhance the magnetic resonance imaging process by providing support for a patient in positions that enhances patient comfort and reduces the potential for patient movement while allowing the patient to be oriented in a position that provides for improved imaging of the region of interest.

SUMMARY OF THE INVENTION

An aspect of the present invention is the provision of a patient positioning apparatus for a magnetic resonance imaging system that is preferably capable of generating a horizontal magnetic field. The apparatus preferably comprises a patient support having a support surface adapted to receive at least one rest member and a first rest member engaged to the patient support and positioned to provide a rest area for a patient's knee or buttocks while the patient's anterior to posterior axis is substantially parallel to the horizontal magnetic field.

Further in accordance with this aspect of the present invention, it is preferable that the support surface includes a pair of slots extending in a longitudinal direction along the patient support. It is further desirable that the support surface includes pairs of pockets disposed within the slots such that each of the pockets forming a pair is disposed laterally along a line perpendicular to the longitudinal direction and wherein each of the first and second rest members are engaged to said patient support by respective pairs of pockets.

Further in accordance with this aspect of the present invention the patient positioning apparatus preferably further comprises a second rest member engaged to the patient support and positioned to provide a rest area for the patient's buttocks and wherein the first rest member provides a rest area for the patient's knees.

It may prove further desirable if the first and second rest members are positioned to support the patient in a substantially upright position such that the patient's weight is distributed between the patient's knees and buttocks.

Still further in accordance with this aspect of the present invention, the first and second rest members are preferably engaged to the support surface through a base plate. In addition, the support surface may include a pair of slots and the base plate includes a pair of suspension hooks engaged to the support surface slots.

It may prove further desirable to have the base plate include a plurality of pairs of slots and the first and second rest members each include a pair of support hooks which are engageable to a pair of the base plate slots.

Further in accordance with this aspect of the present invention, the first and second rest members each preferably comprise a cushiony support surface connected to a base member. It may prove further desirable to have the cushiony surface connected to the base member by an adjustable locking mechanism.

Further in accordance with this aspect of the present invention, the first rest member is preferably adjusted to engage the patient support at another position so to provide a rest area for the patient's buttocks and the second rest member is adjusted to engage the patient support at another position so to provide a rest area for the patient's knees.

It may prove further desirable to have the first and second rest members positioned so that the patient's weight is supported by the patient's buttocks, knees and feet.

Another aspect of the present invention is the provision of an apparatus for positioning a patient to be imaged, preferably, by a magnetic resonance imaging system. The apparatus comprises a patient support having a support surface adapted to receive one or more rest members. The apparatus further preferably includes a first member that is engaged to the patient support surface and positioned so as to provide a rest area for a patient's knee. A second rest member preferably engages the patient support and is positioned to provide a rest area for the patient's buttocks.

In accordance with this latter aspect, the patient support includes a pair of slots extending in a longitudinal direction along the length of the table. Pairs of pockets are disposed within the slots such that each of the first and second members are engaged to the patient support by respective pairs of pockets.

Further in accordance with this aspect of the present invention, the first and second members are positioned so as to support the patient in a substantially upright position such that the patient's weight is distributed between the patient's knees and buttocks.

Further in accordance with a preferred embodiment, the first and second rest members are engaged to the support surface using a base plate. The support surface desirably includes a pair of slots and the base plate includes a pair of suspension hooks engaged to the slots of the support surface. The base plate preferably includes a plurality of pairs of slots and the first and second rest members each include a pair of support hooks which are engaged to a pair of the base plate slots.

In accordance with this aspect, the first rest member can be desirably adjusted to provide a rest area for the patient's buttocks and the second rest member can be desirably adjusted to provide a rest area for the patient's knees.

In another aspect, the invention comprises a magnetic resonance imaging system. The system preferably includes a magnet having a pair of elements spaced apart from one another along a horizontal magnetic field axis and defining a patient-receiving space therebetween. A patient support is preferably disposed within the patient-receiving space and includes a support surface that is adaptable to receive patient support fixtures. Further in accordance with this embodiment, a first support fixture capable of supporting the knees of a patient oriented in a substantially upright position is affixed to the patient support and a second support fixture capable of supporting the buttocks of the patient is affixed to the patient support.

Further in accordance with this aspect of the invention, each of the elements of the system preferably comprises a magnet pole. In accordance with another embodiment, the elements may comprise the field coils of an electromagnet, which may preferably be a superconducting magnet.

Another aspect of the present invention is a method for imaging a patient. The method includes providing a magnet having a pair of elements spaced apart along a horizontal magnetic field axis and defining a patient-receiving space therebetween and positioning a patient in a substantially upright position in the patient receiving space such that the patient's weight is preferably distributed at least between the patient's knees and buttocks.

Further in accordance with this method aspect of the present invention, a substantially horizontal static magnetic field is established between the elements and magnetic resonance signals are elicited by preferably transmitting radio frequency energy to the body of the patient and receiving said magnetic resonance signals.

Yet further in accordance with this method aspect positioning preferably includes providing a patient support apparatus in the patient-receiving space, affixing a knee rest and a seat rest to the patient support apparatus, and using the knee rest and seat rest to position the patient.

Further in accordance with the method it is further desirable to perform kinetic studies of the patient's shoulder area when positioned using the patient support apparatus.

In yet another method aspect of the present invention, a method of positioning a patient for magnetic resonance imaging is provided. The method preferably comprises establishing a horizontal static magnetic field between a pair of elements, positioning a patient on a patient support between the pair of elements such that a portion of the patient's weight is supported by a first fixture connected to the patient support and adjusted to provide a rest area for either the patient's knee or buttocks with the patient's anterior to posterior axis being substantially parallel to the horizontal magnetic field and eliciting magnetic resonance signals by applying radio frequency excitation energy to the patient's body.

In accordance with this latter method aspect, the method further desirably comprises positioning the patient such that a portion of the patient's weight is supported by the patient's feet.

It may prove further desirable to position the patient such that the first fixture is adjusted to provide a rest area for the patient's buttocks and such that a second fixture is adjusted to provide a rest area for the patient's knee.

The method may further desirably include positioning the patient such that a portion of the patient's weight is supported by the patient's feet. The method also may desirably further include performing kinetic studies of the patient's shoulder region.

In accordance with the present invention, the risk of patient movement during imaging is reduced. In addition, by distributing the patient's weight between his/her legs and/or buttocks and/or feet, the patient may be able to undergo imaging even where the patient experiences pain and discomfort from, for example, a back injury. In addition, reducing the probability of patient movement may result in an increase in the number of patients imaged per unit of time as well a more consistent image quality which is free motion artifacts for a system or magnet employing an apparatus in accordance with the present invention.

DETAILED DESCRIPTION

Figure 1:
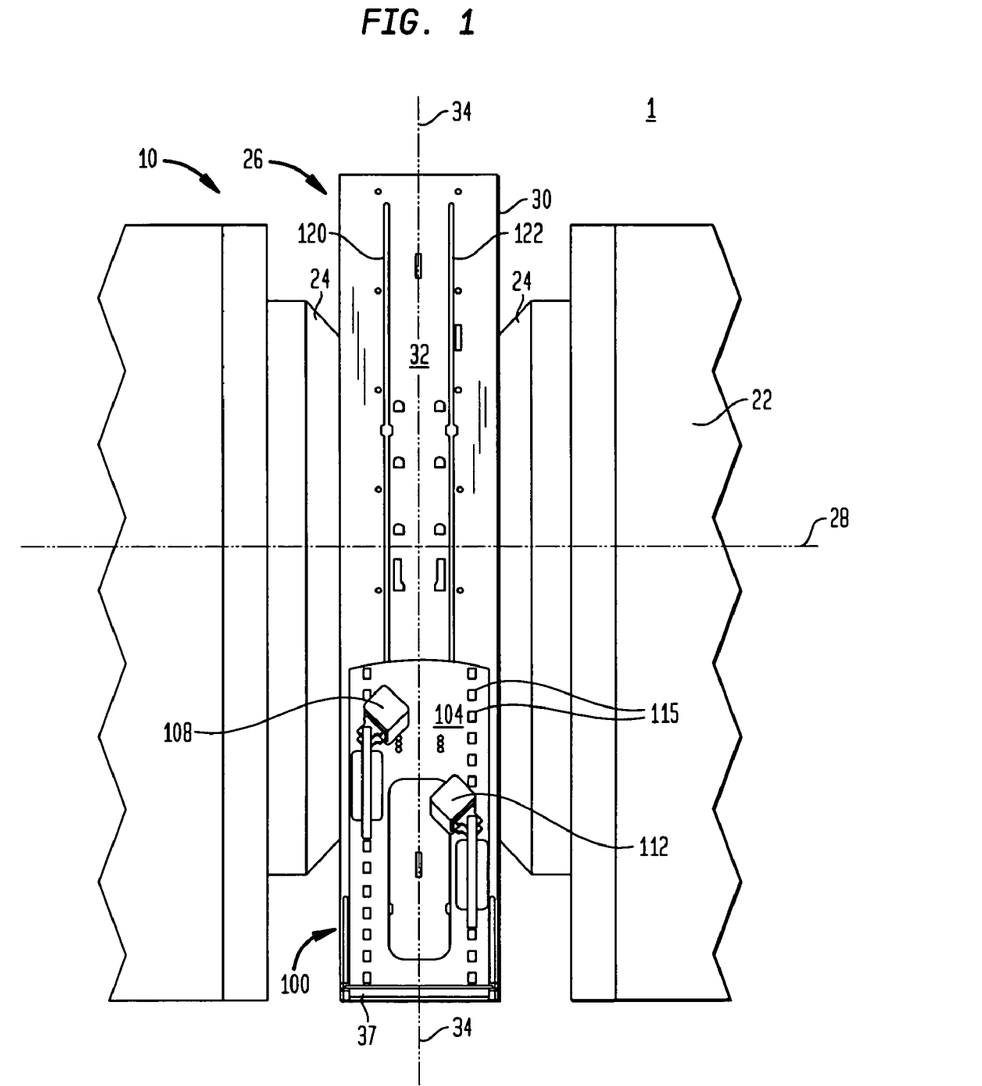
FIG. 1 is a diagrammatic front view of magnetic resonance imaging system in accordance with an embodiment of the invention.

FIG. 1 depicts a front view of magnetic resonance imaging system 1 in accordance with an embodiment of the present invention. The system 1 includes a magnet resonance imaging apparatus 10, which is generally in accordance with the disclosure of the aforementioned commonly assigned U.S. patent and co-pending patent applications, the disclosures of which are incorporated by reference in their entirety herein. The resonance imaging apparatus 10 includes a magnet 22 comprising a pair of opposed elements 24 defining a patient-receiving space 26 between them. In the particular magnet illustrated, the opposed elements are pole faces. Other types of magnets may also be used and may comprise superconducting or resistive electromagnet coils or other structures. The magnet 22 is arranged to provide a magnetic field surrounding a magnet axis 28 within patient-receiving space 26. The magnet axis 28 as well as the magnetic field axis of the magnet extends in a substantially horizontal direction.

The magnetic resonance imaging apparatus 10 further includes a patient support 30 having a patient support surface 32 and a longitudinal direction 34. The patient support surface 32 lies in a generally vertical plane and the longitudinal direction extends generally vertically. However, it is also possible to rotate the patient support 30 so that the longitudinal direction extends in a substantially horizontal direction, or any direction between horizontal and vertical. The widthwise or lateral dimension of the patient-receiving surface is transverse to the longitudinal direction 34 and parallel to the magnet axis 28. The lateral dimension is slightly less than the dimension of the patient-receiving space 26 between the elements 24. A footrest 37 projects from one end of the patient-receiving surface 32 and is generally used as standing surface.

Figure 2A:
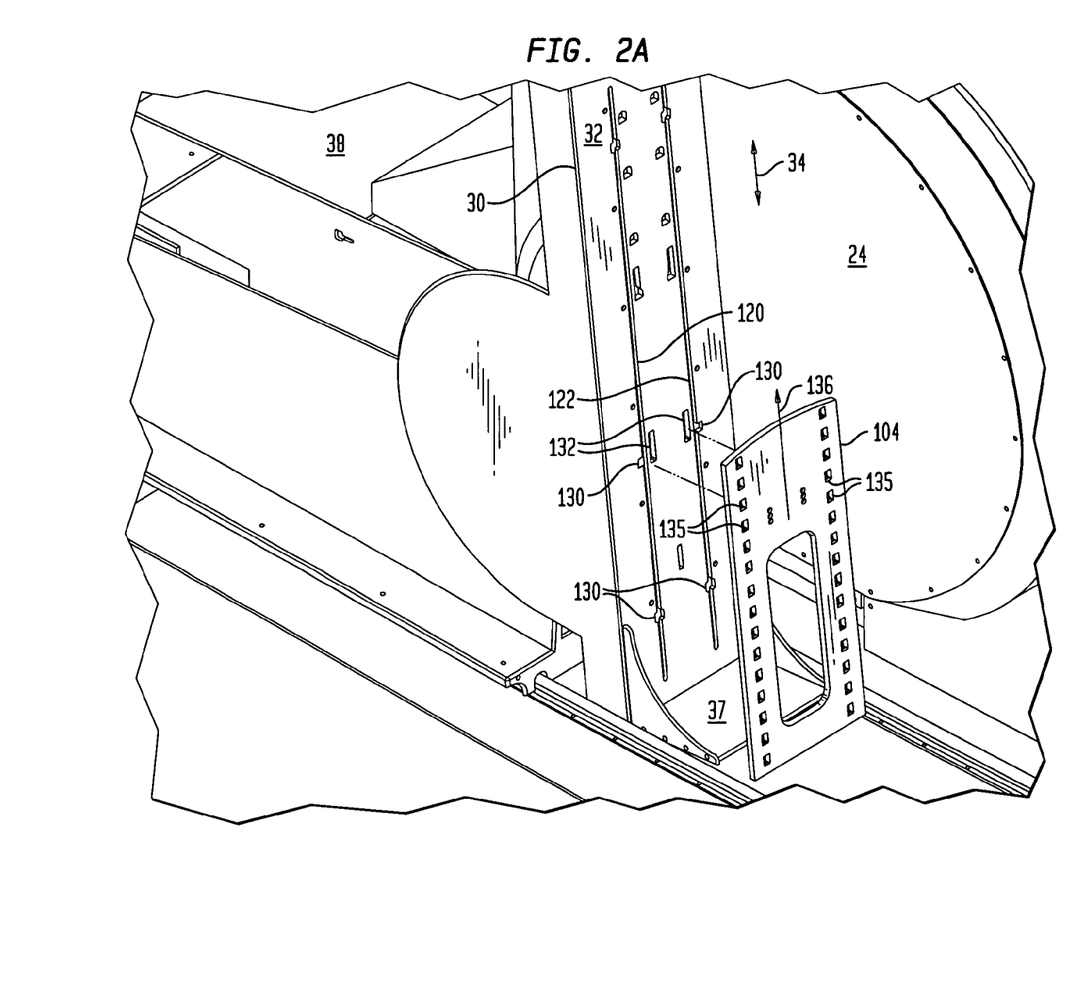
FIGS. 2A and 2B depict exploded views of the support surface and the base plate in accordance with an aspect of the present invention.
Figure 2B:
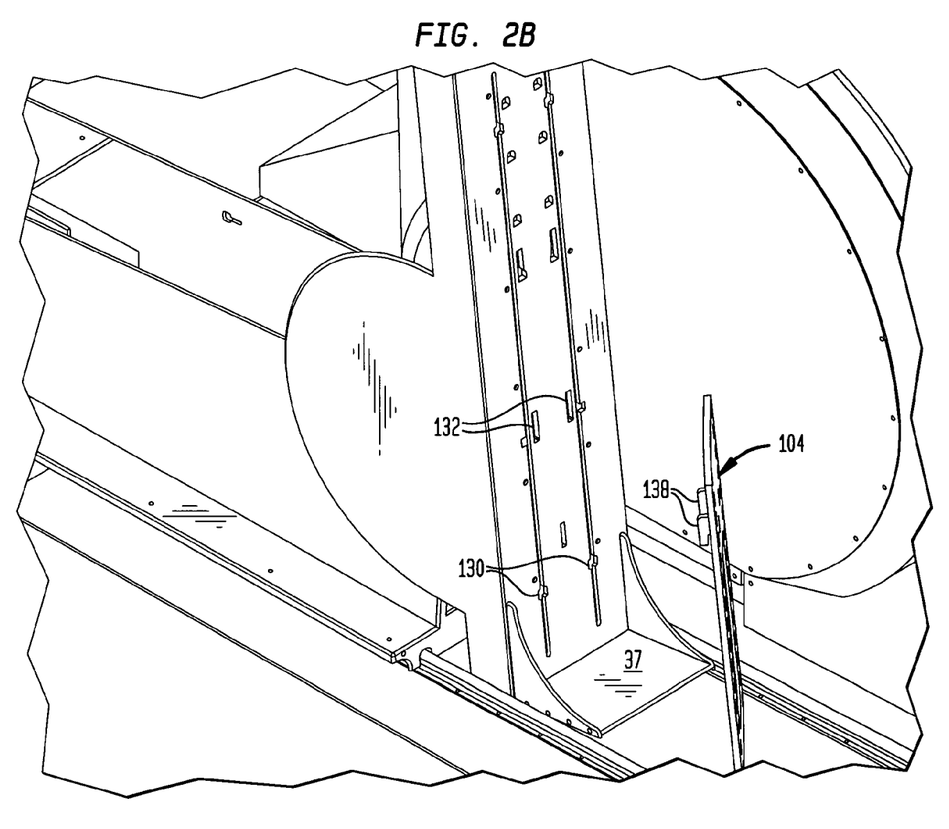

As best seen in FIGS. 2A and 2B, the patient support 30 is associated with a carriage 38 incorporating a drive unit (not shown) arranged to move the patient support in a direction parallel to its longitudinal direction and, as previously discussed, to rotate the support 30 between the vertical condition illustrated and a horizontal condition (not shown) in which the patient-receiving surface 32 and longitudinal direction 34 are generally horizontal. The magnet may also include a rail system for traversing the patient support along a horizontal plane.

As FIG. 1 also shows, an apparatus 100 is engaged or affixed to the patient support 30. The apparatus 100 limits or eliminates the movement of a patient or subject being imaged by allowing the patient to rest his/her body in a substantially upright orientation without requiring the patient to completely stand upright. In addition to enhancing patient comfort, the apparatus 100 allows the legs to be bent at the knees, which causes the blood flow in the leg area to be less restricted than that of someone who is standing erect or completely upright.

The apparatus 100 includes a base plate 104, a first rest member 108 for supporting a patient's buttocks and a second rest member 112 for supporting a patient's knee, i.e., functioning as a seat. We colloquially refer to the apparatus 100 as a "body rest," the first member 108 as a "seat" and the second member 112 as a "knee rest." In the embodiment shown (and as is discussed in further detail below) the first and second members 108 and 112 engage the base plate 104 via slots 115.

Figure 3:
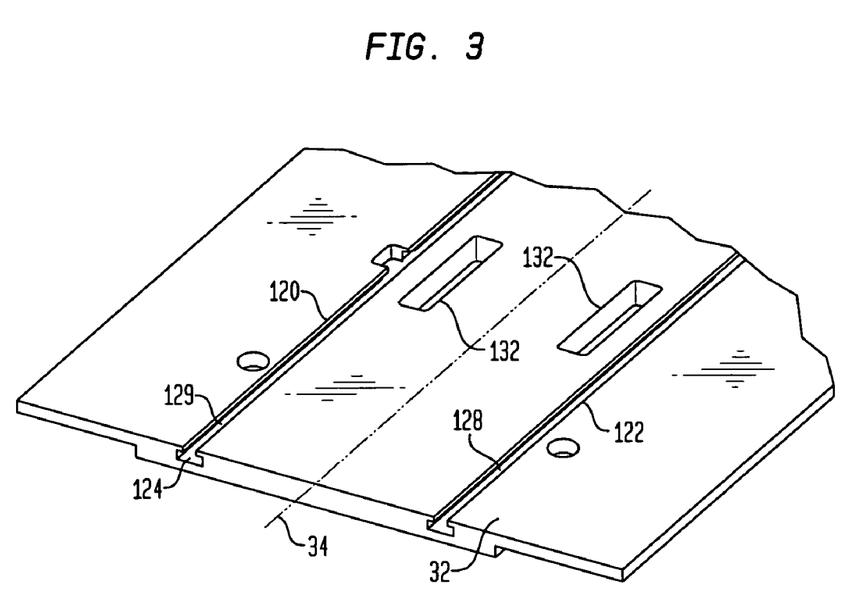
FIG. 3 is an exploded partial view of the support surface of a magnetic resonance imaging apparatus in accordance with an aspect of the present invention.

As best seen in FIGS. 2A and 2B, the patient receiving surface 32 includes a pair of slots 120 and 122 extending parallel to each other in the longitudinal direction 34 of the support 30. As shown in greater detail in FIG. 3, the slots 120 and 122 are generally T-shaped 124 in cross section. Thus, each slot has a narrow top portion 128 where the slots open to the surface 32 remote from the opening of the slot. Pockets 130 (see FIGS. 2A and 2B) are provided in pairs along the lengths of the slots 120 and 122. These pockets are generally wider than the narrow top portion 128. The surface 32 further includes a pair of rectangular slots 132 disposed opposite each other along the lateral direction of the surface 32. In addition to the foregoing, commonly assigned U.S. patent application Ser. No. 10/131,843, the disclosure of which is hereby incorporated by reference, discloses additional methods for connecting structures to the support surface.

The base plate 104 may be constructed from a magnetically translucent material such as plastic or various composite materials although resin fiber is the preferred material. In the embodiment shown the base plate 104 is of a generally rectangular shape and includes a plurality of paired slots 135 that extend along a vertical axis 136 of the plate 104. A pair of suspension hooks 138 project from the rear surface of the plate 104. The hooks 138 are used to engage or affix the back plate to the patient receiving surface 32 of the support 30. As shown, the suspension hooks 138 are L-shaped and of a thickness slightly less than the opening of rectangular slots 132. The hooks 138 are inserted into the slots 132 such that the hooks 138 lock into place. When engaged to the surface 32, the plate 104 provides stability and support for the apparatus 100.

Figure 4A:
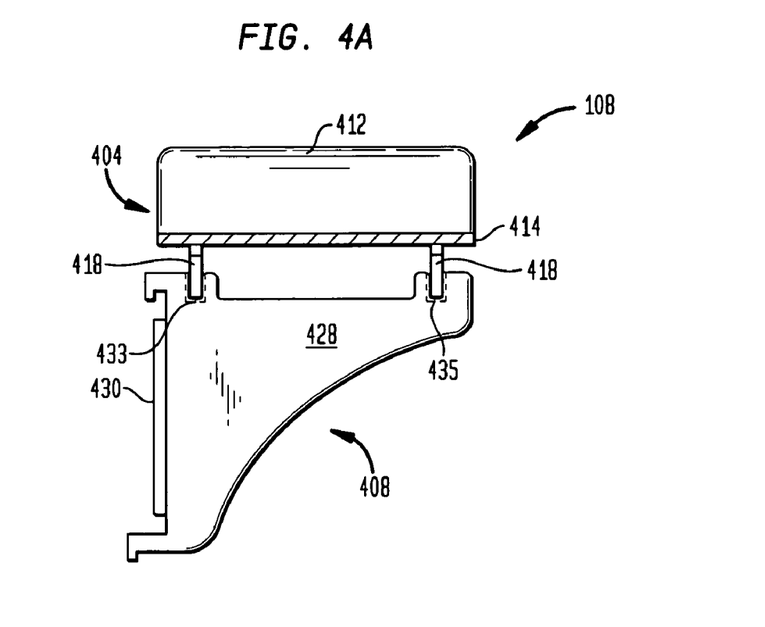
FIGS. 4A and 4B illustrate a seat rest in accordance with an aspect of the present invention.

FIG. 4A illustrates a side view of the first rest member or seat 108. The rest member 108 comprises a seat portion 404 that is connected to a base portion 408. The seat portion 404 includes an upper portion 412 that is constructed from a cushiony material intended to provide comfortable rest area for a patient. The cushiony material may comprise sponge or foam rubber or any other similar materials. The seat portion 404 also includes a rigid base member 414 to which the seat portion is affixed. The base member 414 may be constructed from any number of materials including plastics or wood, as long as the materials are non-magnetic; however, to avoid causing eddy current artifacts in the images obtained, certain electronically conductive materials, even if non-magnetic, may not be suitable for use. A pair of legs 418 project from the base member 414. The legs 418 are positioned to distribute the load supported by the seat portion equally, e.g., positioned at approximately the same distance from the shorter side of each seat, and serve as a connection and/or rotation point for the base portion 408. The legs 408 may be a separate structure from the base member 414 or may form a unitary structure with the base member 414, e.g., where the base member 414 is made from a rigid plastic.

Figure 4B:
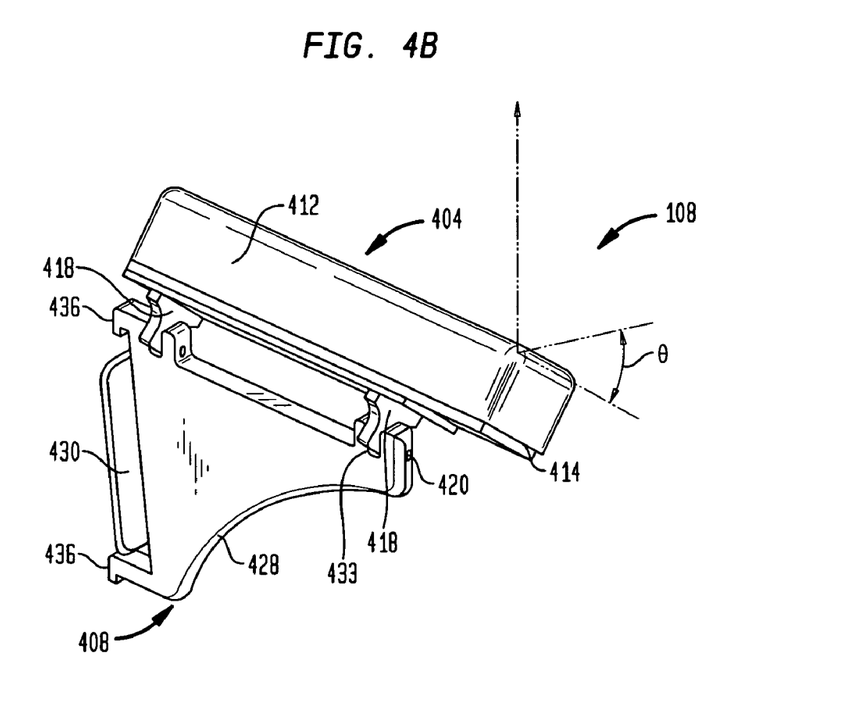

As best seen in FIG. 4B, the legs 418 are essentially Y-shaped with their narrower end having holes tapped therethrough for accepting a fastener 420 that is also threaded through the base portion 408. The fastener 420 may be any number of fasteners including, but not limited to, screws, rivet, pins, locking mechanism, lug, etc. In some instances it may be advantageous to have the seat portion 404 adjustable relative to the base portion 408 so as to allow the seat to tilt to a position that may be more comfortable to a patient. In such instances the fastener may comprise an adjustable locking mechanism that can be loosened and tightened by an operator.

Figure 6A:
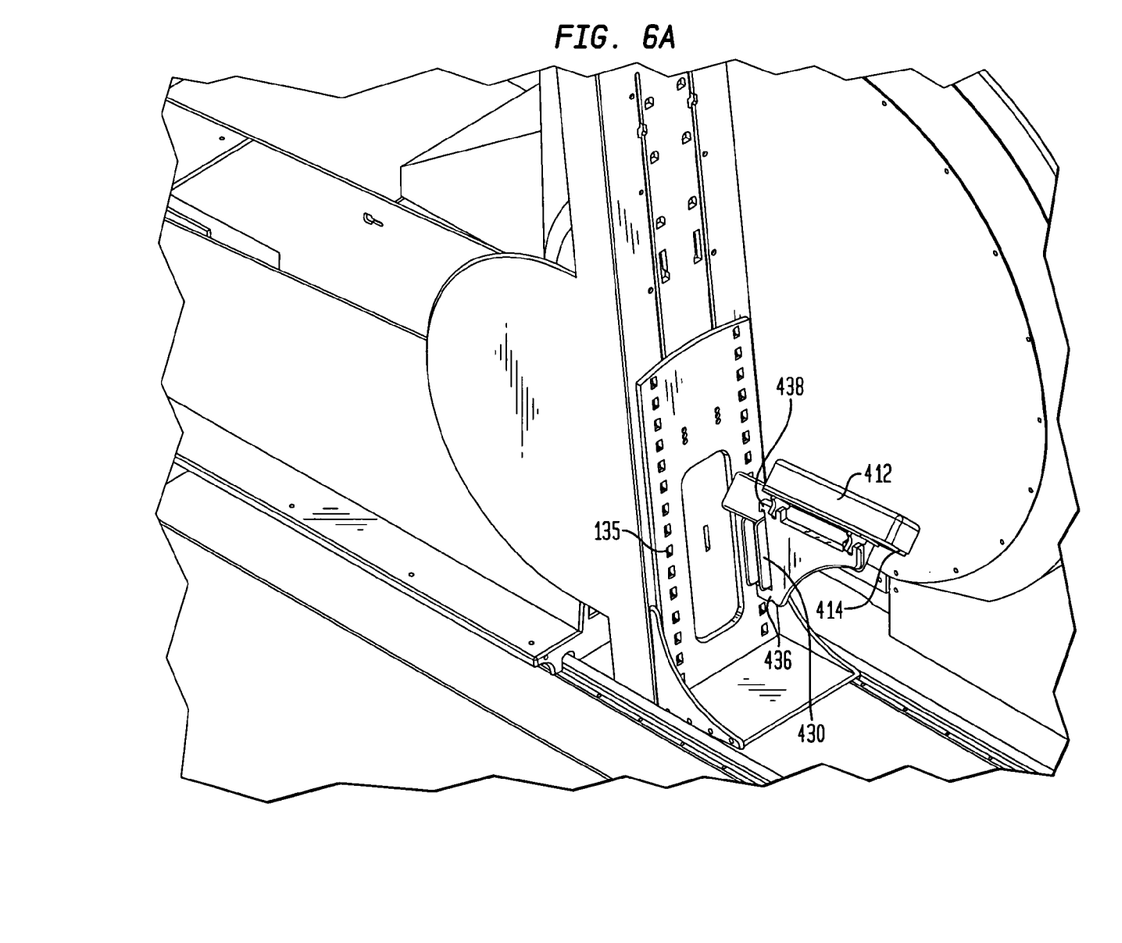
FIGS. 6A and 6B are exploded partial views of the base plate and rests when disengaged and engaged.
Figure 6B:
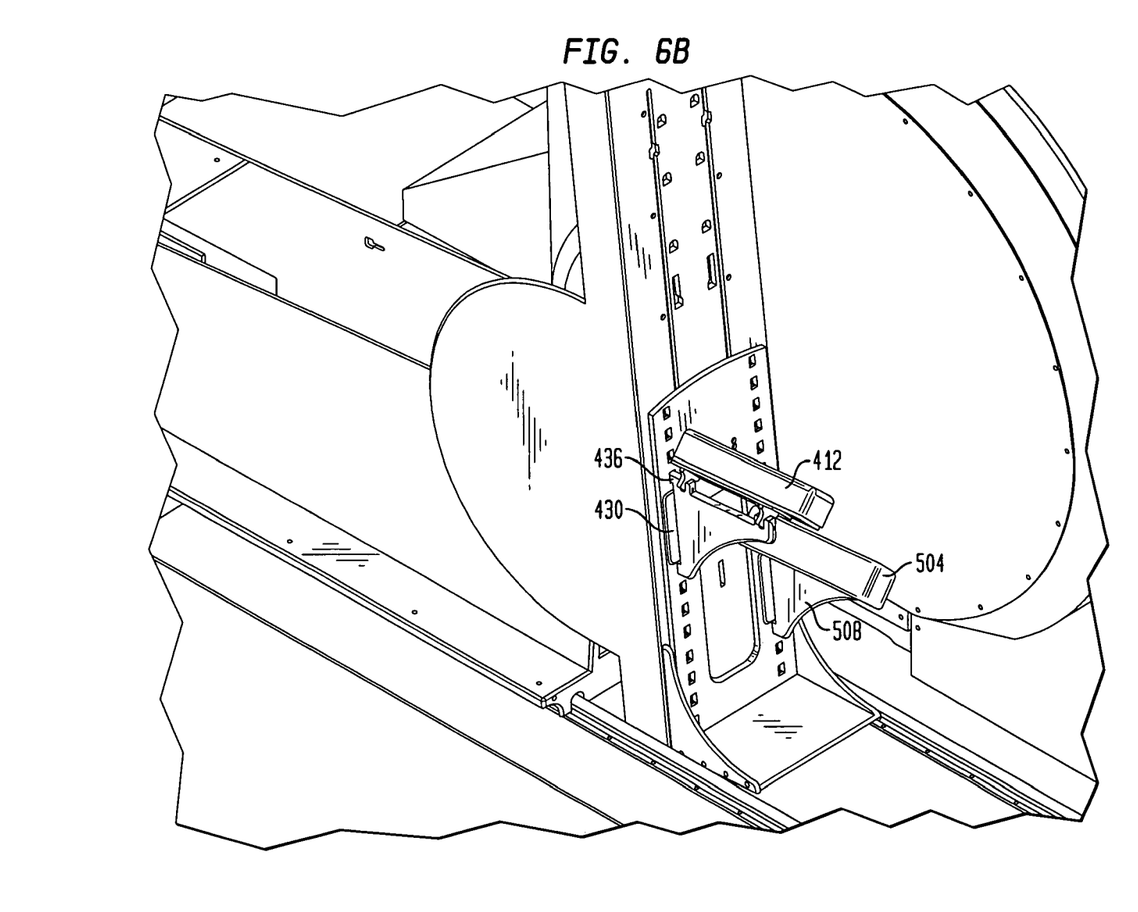

In the embodiment shown, the base member 408 comprises a substantially triangular shaped member 428 and a stabilizing cross-sectional member 430. The member 428 is of a unitary structure and includes a pair of U-shaped recesses 433 into which legs 418 are disposed. The member 428 further includes a pair of hooks 436, which, as best seen in FIGS. 6A and 6B, engage a pair of the slots 135 (on a vertical line) on the base plate 104. The cross-sectional member 430 provides a wider surface area for distributing some of the forces exerted on the base member 408 when supporting a patient. Although the member 430 is shown as being rectangular in shape other shapes, such as circular, oval, square, etc., may also be used to serve the same purpose. In the embodiment shown the member 430 is fastened to the member 428 by a pair of screws (not shown). Other fasteners may also be used.

In addition, during operation the seat portion 404 is preferably fixed at an angle ø relative to a horizontal plane so to comfortably provide a rest area for a patient's buttocks.

Figure 5:
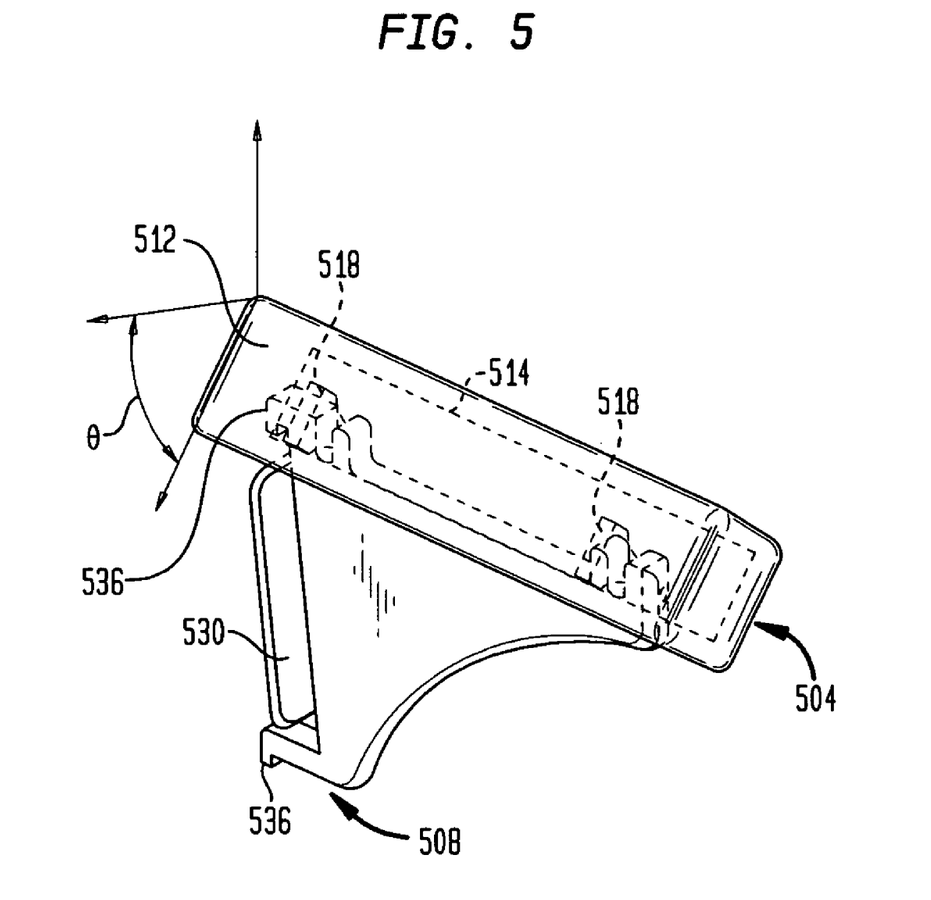
FIG. 5 illustrates a knee rest in accordance with an aspect of the present invention.

Turning now to FIG. 5, there is shown a second member or knee rest 112 in accordance with an aspect of the present invention. The second member 112 is constructed in a similar fashion to the first member 108. However, in the embodiment shown the angle of tilt θ is oriented in a direction opposite that of the angle ø. In this way, the first member is oriented to support the knees of a kneeling patient. The second member 112 includes rest portion 504 that is connected to a base portion 508. The rest portion 504 includes an upper portion 512 that is also constructed from a cushiony material that provides comfortable support to the knees of a kneeling patient. The rest portion 504 includes a rigid base member 514 to which the rest portion is affixed. A pair of legs 518, similar to legs 418, also project from the base member 514 and are positioned to share the load of a kneeling patient.

The base portion 508 comprises a substantially triangular shaped member 528 and a stabilizing cross-sectional member 530. Both these members may be constructed as described above in relation to members 428 and 430. In addition, the first member 108 engages the base plate 104 at a pair of vertically aligned slots 135 via hooks 536. As in the case of the first member 108, the second member 112 also includes a stabilizing member 530.

As previously noted, FIGS. 6A and 6B show partial exploded views intended to illustrate the members 108, 112 and base plate 104 in a disengaged and engaged position. In the embodiment shown, the first member 108 is positioned at higher elevation than the second member 112. In this way, the first member 108 provides a rest area for a patient's buttocks and functions as a seat. The second member 112 provides a rest area for the patient's knees. In this position a patient's weight is distributed between his or her knees, feet and buttocks. This position is known to be more "ergonomic" and reduces the stress on the back of a patient and causes the blood flow in leg area to be less restricted than if the patient were standing. This results in patients being more comfortable, which ultimately leads to less movement during the imaging process. As previously noted, reduction in patient movement during imaging may result in a higher throughput a more consistent image quality which is free from motion artifacts. In addition, ergonomic positioning of a patient may aid in yielding images that allow for better prognosis or diagnosis.

Figure 7A:
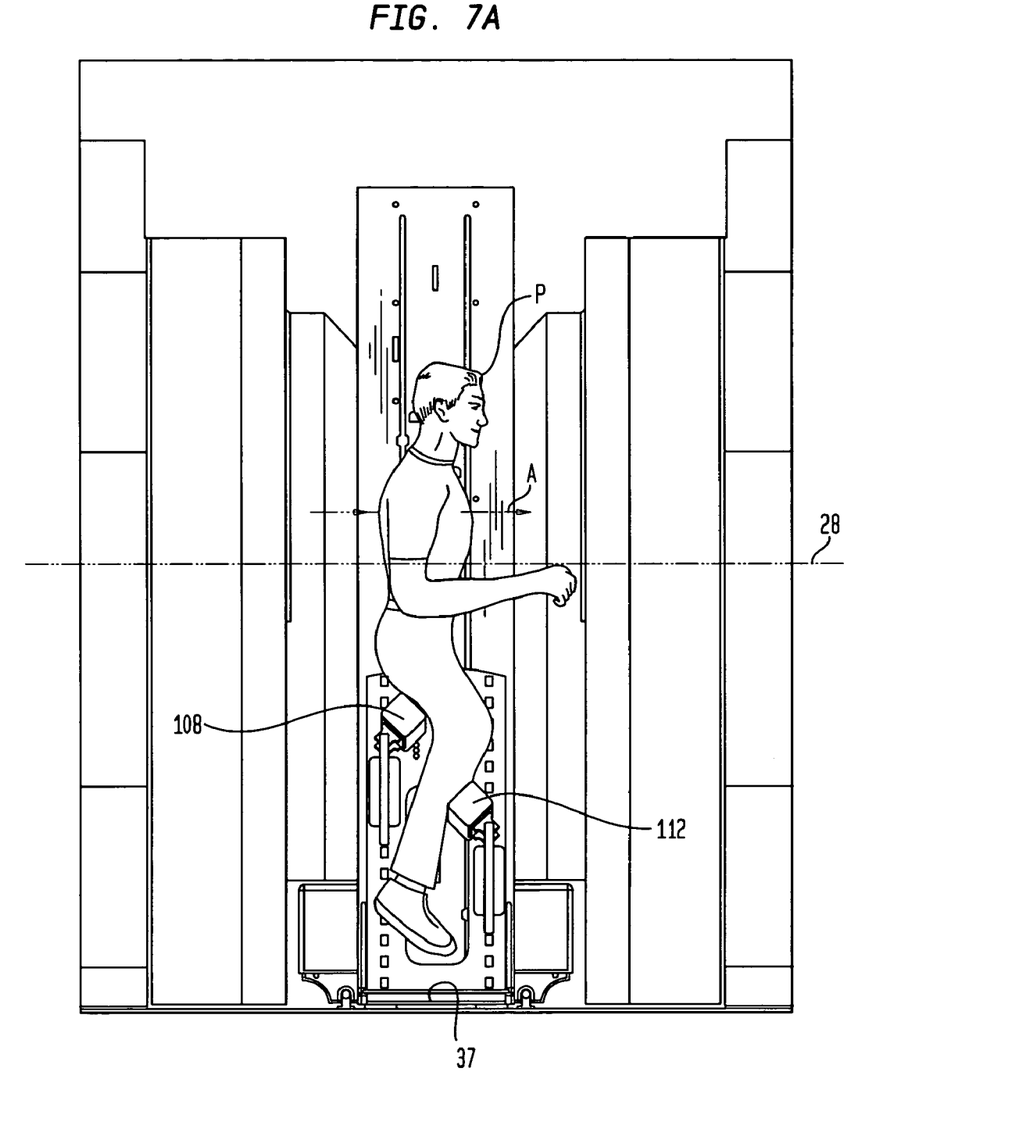
FIGS. 7A and 7B illustrate patient imaging in accordance with embodiments of the present invention.
Figure 7B:
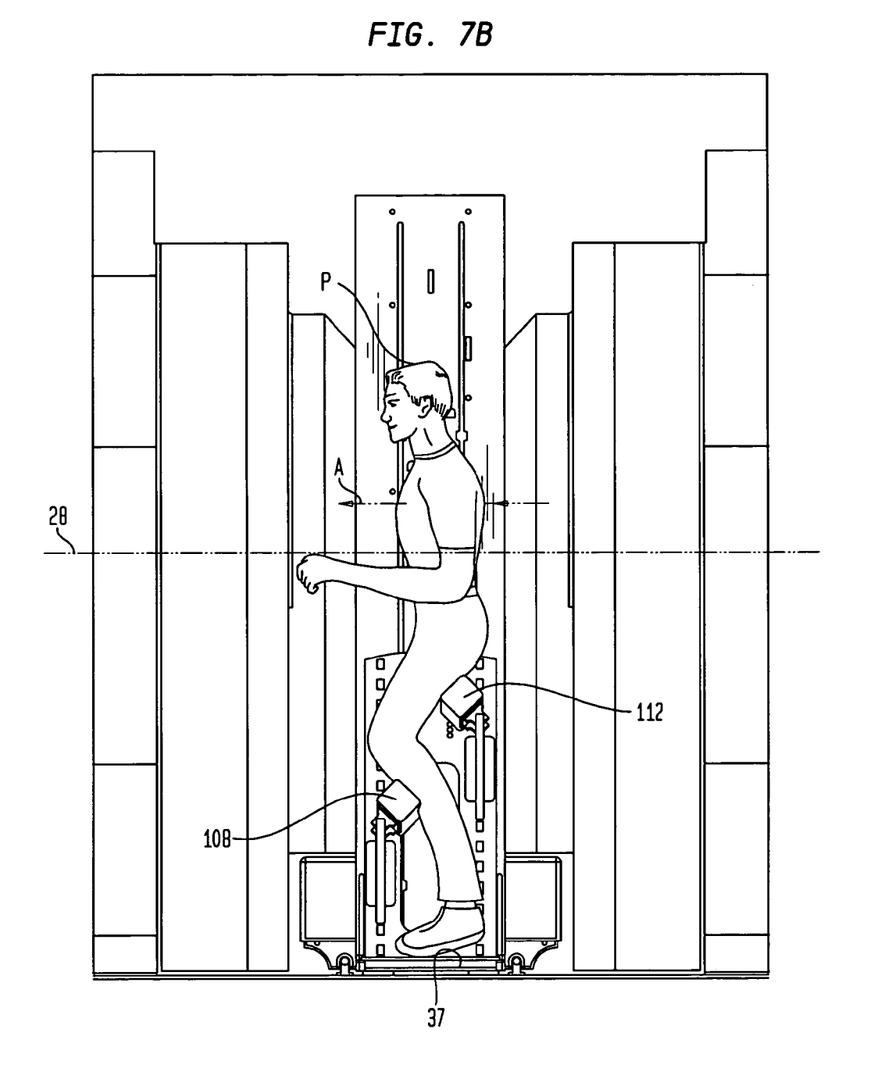

FIGS. 7A and 7B depict a patient P being imaged in accordance with an aspect of the present invention with the anterior to posterior axis A of the patient P being oriented generally parallel to the direction of the static magnetic field and magnet axis 28. In FIG. 7A the patient P is oriented with their right shoulder pointing out the patient receiving space of the magnetic resonance imaging apparatus 10. The patient knees are bent and the patient's legs are shown resting against the knee rest 112. In accordance with the flexibility afforded by the apparatus 100, if the patient would find it more comfortable with his/or her knees resting against the knee rest 112, then the knee rest 112 can be raised or the seat 108 lowered so that the patient's knees rest against the knee rest 112. The patient's buttocks are shown as being supported by the seat 108. In this position the patient's weight is distributed between his/her knees and buttocks. It is also possible to adjust the seat 108 and knee rest 112 such that the patient's feet also rest against the foot rest 37. In this orientation the patient's weight would be distributed between the patient's feet, knees and buttocks.

In FIG. 7B the patient P is oriented with his/her left shoulder pointing out the patient receiving space of the magnetic resonance imaging apparatus 10. In contrast to FIG. 7B, the first member 108 (which functioned as a seat in FIG. 7A) now functions as a knee rest and the second member 112 (which functioned as a knee rest in FIG. 7A)

now functions as a seat. In accordance with an aspect of the present invention, in adjusting the body rest to support the patient's position shown in FIG. 7B the first member 108 is lowered and the second member 112 is elevated. Thus, the first and second members, 108 and 112, advantageously function as either a seat or knee support depending on their relative attachment points along the plate 104. This offers additional versatility to the device as these two members support both the orientations shown in FIGS. 7A and 7B. It is also possible to adjust the seat 108 and knee rest 112 such that the patient's feet also rest against the foot rest 37 (as shown in FIG. 7B). In this orientation the patient's weight would be distributed between the patient's feet, knees and buttocks.

Further in accordance with this aspect of the present invention, by orienting the patient in the positions shown in FIGS. 7A and 7B, kinetic or kinematic studies of the patient's free shoulder may be performed. In general, a person standing fully erect, i.e., completely supporting their body weight with their feet, cannot remain still enough to perform kinetic studies of the patient's shoulder. Thus, in accordance with FIGS. 7A and 7B a kinetic study of the free (or outward projecting) shoulder of the patient may be advantageously performed. Further in this regard, a kinetic study of either shoulder may be performed by changing the orientation of the patient so that either the left or right shoulder is free or projects out of the patient receiving space. A kinetic or kinematic study in accordance with the present invention includes imaging the position of a movable joint of a patient in a plurality of predetermined positions. For example, in accordance with an aspect of the present invention, the shoulder of a patient may be imaged while the patient's arm is at his/her side. Next, the patient's arm may be positioned such that it is extended parallel to the floor. The patient's shoulder may then be imaged in this latter position. Imaging with the patient's arm in other positions may also be done to obtain images of the area of interest while the patient's arm is in various positions. Additional details relating to kinematic studies using MRI are disclosed in U.S. Pat. No. 5,899,859, which is assigned to the assignee of the present application and the disclosure of which is incorporated by reference herein in its entirety.

It may also prove further desirable to position the patient using only the knee rest 112, so that the patient's weight is supported by his/her knees and feet. That is, the seat would be not used in this particular aspect of the present invention. It may prove further desirable to position the patient using only the seat 108 and the patient's feet during some imaging procedures. Accordingly, the seat 108 and foot rest 112 may used either together or independently to support a patient in many different desirous positions depending on the scanning information desired.

In a variant to the apparatus 100, the support surface 32 of the patient support 30 may be constructed to directly receive the first and second members 108 and 112. In such an embodiment, a series of paired slots, similar in construct to those shown for the base plate 104, may be directly formed in the support surface 32. In this way, the first and second members 108 and 112 would then be directly inserted and adjusted to support either the right shoulder-out or left shoulder-out orientation of a patient as described above. It is also possible to design members 108 and 112 so that they are housed and locked into slots 124 and 128 of the support surface 32. In such an embodiment, the slots 124 and 128 may include a larger opening to receive the hooks or connection points of the rest members 108 and 112. The members 108 and 112 could also be inserted in pockets 130 and locked into place.

In a further variant to the embodiment shown, it is possible to construct a device with less versatility by having fewer slots for receiving the first and second members. Indeed, it may be possible to have two or three pairs of slots that allow the rest members 108 and 112 two or three possible locations along the longitudinal direction 34 of the support 30.

As previously mentioned in constructing the apparatus additional measures can be provided to enhance patient comfort, for example, by allowing of adjustment of the angles θ or ø through the use of a locking mechanism to connect the cushioned portion of a rest to its base member.

In addition, in some applications it may prove useful to adjust the position of the first and second members such that a portion of the patient's weight is supported by a footrest, such as footrest 37.

Although the invention herein has been described with reference to particular embodiments, it is to be understood that these embodiments are merely illustrative of the principles and applications of the present invention. In particular, the principles of the present invention may be employed in any apparatus capable of performing magnetic resonance imaging of a patient in a substantially upright position. In addition, the principles of the present invention are applicable where a patient is being scanned by other imaging methods, e.g., CAT scan, X-ray, etc. It is therefore to be understood that numerous modifications may be made to the illustrative embodiments and that other arrangements may be devised without departing from the spirit and scope of the present invention as defined by the appended claims.

The invention claimed is:

1. A patient positioning apparatus for a magnetic resonance imaging system, the system being capable of generating a horizontal magnetic field, comprising:
   a patient support having a support surface adapted to receive at least one rest member; and
   a first rest member engaged to said patient support and positioned to provide a rest area for a patient's knee or buttocks while the patient's anterior to posterior axis is substantially parallel to the horizontal magnetic field,
   wherein said support surface includes a pair of slots extending in a longitudinal direction along the patient support and pairs of pockets disposed within said slots such that each of the pockets forming a pair is disposed laterally along a line perpendicular to the longitudinal direction and wherein each of said first and second rest members are engaged to said patient support by respective pairs of pockets.

2. The apparatus of claim 1 further comprising a second rest member engaged to said patient support and positioned to provide a rest area for the patient's buttocks and wherein the first rest member provides a rest area for the patient's knees.

3. The apparatus of claim 2 wherein said first and second rest members are positioned to support the patient in a substantially upright position such that the patient's weight is distributed between the patient's knees and buttocks.

4. The apparatus of claim 2 wherein said first and second rest members are engaged to said support surface through a base plate.

5. The apparatus of claim 4 wherein said support surface include a pair of slots and said base plate includes a pair of suspension hooks engaged to said support surface slots.

6. The apparatus of claim 5 wherein said base plate includes a plurality of pairs of slots and said first and second rest members each include a pair of support hooks which are connectable to a pair of said base plate slots.

7. The apparatus of claim 2 wherein said first and second rest members each comprise a cushiony support surface connected to a base member.

8. The apparatus of claim 7 wherein said cushiony support surface is connected to said base member by an adjustable locking mechanism.

9. The apparatus of claim 2 wherein said first rest member is adjusted to engage said patient support at another position so to provide a rest area for the patient's buttocks and wherein said second rest member is adjusted to engage said patient support at another position so to provide a rest area for the patient's knees.

10. The apparatus of claim 2 wherein said first and second rest members are adjusted so that the patient's weight is supported by the patient's buttocks, knees and feet.

11. The apparatus of claim 1 further comprising a second rest member engaged to said patient support and positioned to provide a rest area for the patient's knee and wherein the first rest member provides a rest area for the patient's buttocks.

12. The apparatus of claim 11 wherein said first and second rest members are positioned to support the patient in a substantially upright position such that the patient's weight is distributed between the patient's knees and buttocks.

13. The apparatus of claim 11 wherein said first rest member is adjusted to engage said patient support at another position so to provide a rest area for the patient's knees and wherein said second rest member is adjusted to engage said patient support at another position so to provide a rest area for the patient's buttocks.

14. The apparatus of claim 11 wherein said first and second rest members are adjusted so that the patient's weight is supported by the patient's buttocks, knees and feet.

15. A patient positioning apparatus for magnetic resonance imaging, comprising:
 a patient support having a support surface adapted to receive at least two rest members and a patient in a substantially upright position;
 a first rest member engaged to said patient support and positioned to provide a rest area for a patient's knee; and
 a second rest member engaged to said patient support and positioned to provide a rest area for the patient's buttocks.

16. The apparatus of claim 15 wherein said support surface includes a pair of slots extending in a longitudinal direction along the patient support and pairs of pockets disposed within said slots such that each of the pockets forming a pair is disposed laterally along a line perpendicular to the longitudinal direction and wherein each of said first and second rest members are engaged to said patient support by respective pairs of pockets.

17. The apparatus of claim 16 wherein said first and second rest members are positioned to support the patient in a substantially upright position such that the patient's weight is distributed between the patient's knees and buttocks.

18. The apparatus of claim 16 wherein said first and second rest members are adjusted so that the patient's weight is supported by the patient's buttocks, knees and feet.

19. The apparatus of claim 16 wherein said first rest member is adjusted to engage said patient support at another position so to provide a rest area for the patient's buttocks and wherein said second rest member is adjusted to engage said patient support at another position so to provide a rest area for the patient's knees.

20. The apparatus of claim 16 wherein said first and second rest members each comprise a cushiony support surface connected to a base member.

21. A magnetic resonance imaging system, comprising:
 a magnet having a pair of elements spaced apart from one another along a horizontal magnetic field axis and defining a patient-receiving space there between;
 a patient support disposed within said patient-receiving space, said patient support having a support surface that is adaptable to receive patient support fixtures;
 a first support fixture connectable to said patient support in a position capable of supporting the knees of a patient oriented in a substantially upright position; and
 a second support fixture connectable to said patient support in a position capable of supporting the buttocks of the patient.

22. The system of claim 21 wherein each of said elements comprise the poles of a magnet.

23. The system of claim 21 wherein each of said elements comprise the field coils of an electromagnet.

24. The system of claim 23 wherein the electromagnet is a superconducting magnet.

25. The system of claim 21 wherein said magnet comprises a resistive magnet.

26. The system of claim 21 wherein said first and second support fixtures are positioned to support the patient in a substantially upright position such that the patient's weight is distributed between the patient's knees and buttocks.

27. The system of claim 21 further comprising a base plate having a plurality of pairs of slot and a pair of hooks, and wherein said patient support surface includes a pair of pockets and said first and second support fixtures each have a pair of hooks for engaging with respective pairs of slots on said base plate and said hooks of said base plate engage said support surface pockets.

28. A method of positioning a patient for magnetic resonance imaging, comprising:
 providing a magnet having a pair of elements spaced apart along a horizontal magnetic field axis and defining a patient-receiving space therebetween; and
 positioning a patient in a substantially upright position in the patient receiving space such that the patient's weight is distributed at least between the patient's knees and buttocks.

29. The method of claim 28 further comprising:
 establishing a substantially horizontal static magnetic field between the elements; and
 eliciting magnetic resonance signals by transmitting radio frequency energy to the body of the patient and receiving said magnetic resonance signals.

30. The method of claim 29 wherein positioning includes providing a patient support apparatus in the patient-receiving space, affixing a knee rest and a seat rest to the patient support apparatus, and using the knee rest and seat rest to position the patient.

31. The method of claim 28 further comprising performing kinetic studies of the patient's shoulder area.

32. The method of claim 28 further comprising positioning the patient such that the patient's weight is distributed between the patient's knees, buttocks and feet.

33. A method of positioning a patient for magnetic resonance imaging, comprising:
 establishing a horizontal static magnetic field between a pair of elements;

positioning a patient on a patient support between the pair of elements such that a portion of the patient's weight is supported by a first fixture connected to the patient support and adjusted to provide a rest area for either the patient's knee or buttocks with the patient's anterior to posterior axis being substantially parallel to the horizontal magnetic field; and eliciting magnetic resonance signals by applying radio frequency excitation energy to the patient's body.

34. The method of claim 33 further comprising positioning the patient such that a portion of the patient's weight is supported by the patient's feet.

35. The method of claim 33 further comprising positioning the patient such that the first fixture is adjusted to provide a rest area for the patient's buttocks and such that a second fixture is adjusted to provide a rest area for the patient's knee.

36. The method of claim 35 further comprising positioning the patient such that a portion of the patient's weight is supported by the patient's feet.

37. The method of claim 33 further comprising performing kinetic studies of the patient's shoulder region.

* * * * *